(12) United States Patent
Libbus et al.

(10) Patent No.: US 11,786,740 B2
(45) Date of Patent: *Oct. 17, 2023

(54) ASSESSMENT SYSTEM WITH WAND DETECTION CABLE SYNCHRONIZING ECG RECORDING

(71) Applicant: LivaNova USA, Inc., Houston, TX (US)

(72) Inventors: Imad Libbus, St. Paul, MN (US); Scott R. Stubbs, Maple Grove, MN (US); Scott Mazar, Woodbury, MN (US); Bruce KenKnight, Maple Grove, MN (US); Badri Amurthur, Los Gatos, CA (US)

(73) Assignee: LIVANOVA USA, INC., Houston, TX (US)

( * ) Notice: Subject to any disclaimer, the term of this patent is extended or adjusted under 35 U.S.C. 154(b) by 1 day.

This patent is subject to a terminal disclaimer.

(21) Appl. No.: 17/055,015

(22) PCT Filed: May 13, 2019

(86) PCT No.: PCT/US2019/031994
§ 371 (c)(1),
(2) Date: Nov. 12, 2020

(87) PCT Pub. No.: WO2019/222088
PCT Pub. Date: Nov. 21, 2019

(65) Prior Publication Data
US 2021/0213282 A1 Jul. 15, 2021

Related U.S. Application Data

(60) Provisional application No. 62/672,019, filed on May 15, 2018.

(51) Int. Cl.
*A61N 1/365* (2006.01)
*A61N 1/39* (2006.01)

(52) U.S. Cl.
CPC ......... *A61N 1/365* (2013.01); *A61N 1/39622* (2017.08)

(58) Field of Classification Search
None
See application file for complete search history.

(56) References Cited

U.S. PATENT DOCUMENTS 7,103,414 B1 9/2006 Poore et al.
8,239,028 B2 8/2012 Scott
(Continued)

FOREIGN PATENT DOCUMENTS

CN  105009315 A  10/2015
WO  WO-2007/115118 A1  10/2007
WO  WO-2013/086163 A1  6/2013

OTHER PUBLICATIONS

International Search Report and Written opinion on PCT/US2019/031994 dated Jul. 24, 2019. 9 pages.
(Continued)

*Primary Examiner* — Erica S Lee
*Assistant Examiner* — Elizabeth K So
(74) *Attorney, Agent, or Firm* — FOLEY & LARDNER LLP

(57) ABSTRACT

An assessment system is provided for a subject patient implanted with a neurostimulator configured to deliver a stimulation signal having a plurality of ON-periods and OFF-periods. The assessment system includes a wand assembly configured to generate a delivery detection signal indicating delivery of an initiating pulse. The assessment system also includes a processor and a memory associated with the wand. The memory stores instructions that, when
(Continued)

executed by the processor, cause the assessment system to record an ECG signal over at least one successive pair of ON- and OFF-periods and determine changes in heart rate dynamics to indicate autonomic response to the stimulation. The wand assembly includes a programming device configured to wirelessly communicate with the neurostimulator and a cable connector configured to form a surface contact with the programming device. The cable connector includes a detection circuit configured to indirectly detect a time of the initiating pulse.

10 Claims, 13 Drawing Sheets

(56) References Cited

U.S. PATENT DOCUMENTS

| | | |
|---|---|---|
| 9,079,034 B2 | 7/2015 | Milbocker |
| 2003/0040774 A1 | 2/2003 | Terry et al. |
| 2005/0182755 A1 | 8/2005 | Tran |
| 2006/0241725 A1 | 10/2006 | Libbus et al. |
| 2007/0027496 A1 | 2/2007 | Parnis et al. |
| 2007/0255330 A1 | 11/2007 | Lee et al. |
| 2008/0118126 A1 | 5/2008 | Sakaguchi |
| 2008/0140141 A1 | 6/2008 | Ben-David et al. |
| 2010/0191304 A1 | 7/2010 | Scott |
| 2010/0274308 A1 | 10/2010 | Scott |
| 2012/0083700 A1 | 4/2012 | Osorio |
| 2012/0185007 A1 | 7/2012 | Ziegler et al. |
| 2013/0158618 A1 | 6/2013 | Libbus et al. |
| 2013/0253616 A1 | 9/2013 | Libbus et al. |
| 2014/0364921 A1 | 12/2014 | Legay et al. |
| 2015/0073237 A1 | 3/2015 | Osorio |
| 2015/0306395 A1 | 10/2015 | Libbus et al. |
| 2015/0374983 A1 | 12/2015 | Simon et al. |
| 2016/0038754 A1 | 2/2016 | Adjouadi et al. |
| 2016/0101289 A1 | 4/2016 | Stolen et al. |
| 2016/0158554 A1 | 6/2016 | Graig |
| 2016/0339242 A1 | 11/2016 | Cook et al. |
| 2019/0247664 A1* | 8/2019 | Irazoqui ............. A61N 1/36007 |
| 2020/0345251 A1 | 11/2020 | Falk et al. |

OTHER PUBLICATIONS

EP Search Report on EP Appl. Ser. No. 19803136.1 dated Jan. 31, 2022 (5 pages).
CN First Office Action for CN Appl. Ser. No. 201980003312.9 dated Jun. 10, 2020 (11 pages).
CN Second Office Action on CN Appl. Ser No. 201980003312.9 dated Dec. 30, 2020 (8 pages).
EP Office Action on EP Appl. Ser. No. 19802790.6 dated Feb. 17, 2022 (1 page).
EP Search Report on EP Appl. Ser. No. 19802790.6 dated Jan. 31, 2022 (10 pages).
EP Search Report on EP Appl. Ser. No. 19803063.7 dated Jan. 28, 2022 (10 pages).
EP Supplementary Search Report on EP Appl. Ser. No. 19803728.5 dated Jan. 25, 2022 (10 pages).
International Search Report and Written Opinion for PCT Appl. Ser. No. PCT/US2019/031992 dated Jul. 22, 2019. (9 pages).
International Search Report and Written Opinion on PCT Appl. Ser. No. PCT/US2019/031991 dated Jul. 29, 2019 (10 pages).
International Search Report and Written Opinion on PCT Appl. Ser. No. PCT/US2019/031997 dated Jul. 26, 2019 (10 pages).
Libbus et al., "Quantitative evaluation of heartbeat interval time series using Poincare analysis reveals distinct patterns of heart rate dynamics during cycles of vagus nerve stimulation in patients with heart failure," Journal of Electrocardiology, Jun. 8, 2017, vol. 50, No. 6 (pp. 898-903) p. 900, left-hand column; figure 2*.

* cited by examiner

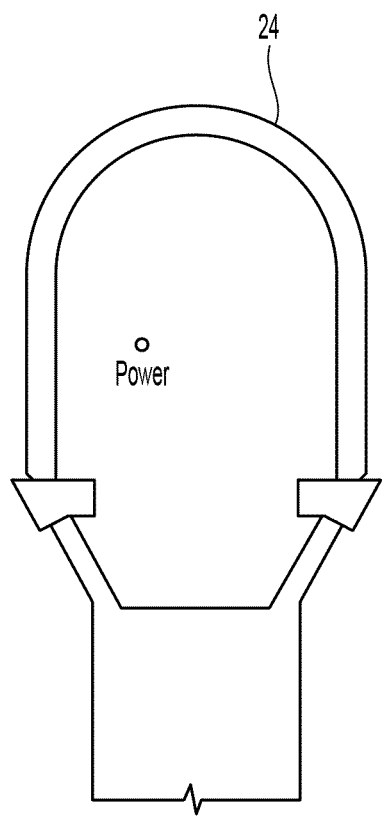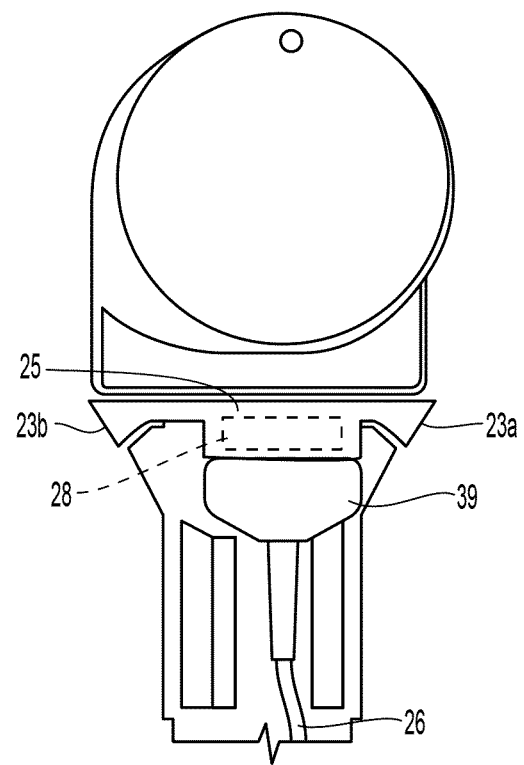
Fig. 6A     Fig. 6B
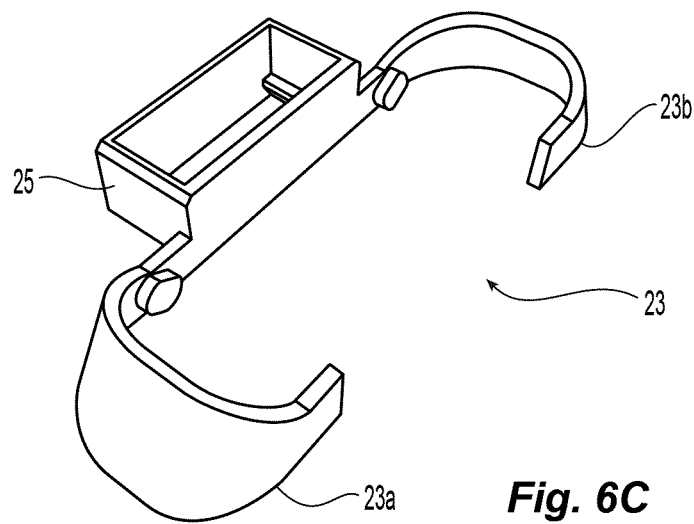
Fig. 6C

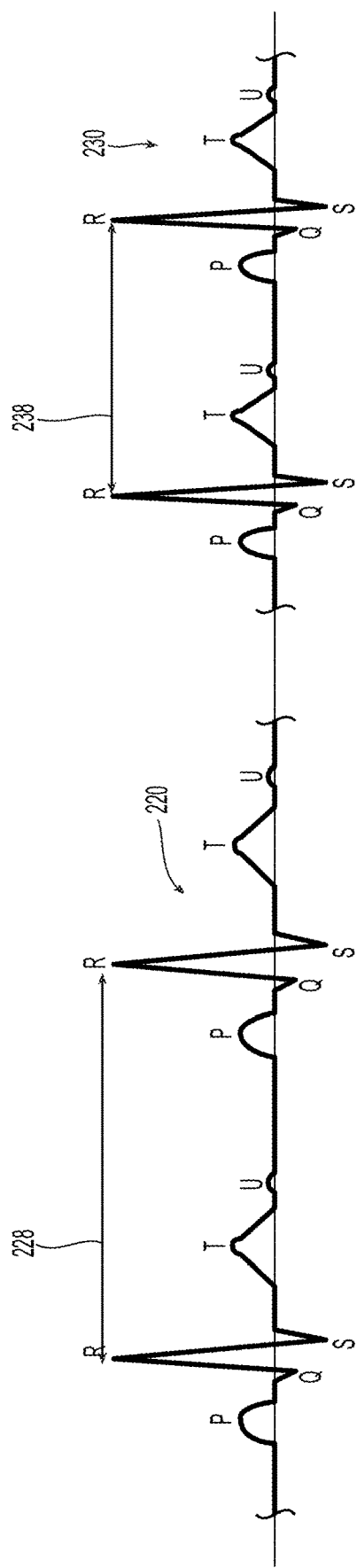

ASSESSMENT SYSTEM WITH WAND DETECTION CABLE SYNCHRONIZING ECG RECORDING

CROSS-REFERENCE TO RELATED PATENT APPLICATIONS

This application is a U.S. National Stage Application of PCT/US2019/031994, filed May 13, 2019, which claims the benefit of and priority to U.S. Provisional Patent Application No. 62/672,019, entitled "ASSESSMENT SYSTEMS AND METHODS USING A WAND DETECTION CABLE TO SYNCHRONIZE ECG RECORDING WITH VAGUS NERVE STIMULATION IN THE TREATMENT OF CONGESTIVE HEART FAILURE," filed May 15, 2018, which is incorporated herein by reference in its entirety.

TECHNICAL FIELD

The present disclosure relates generally to systems and method of neurostimulation therapy and, in particular, to systems and methods for recording a physiological response to vagus nerve stimulation therapy in the treatment of congestive heart failure.

BACKGROUND

Autonomic regulation neurostimulation therapy delivered by vagus nerve stimulation ("VNS") is a treatment for congestive heart failure. VNS therapy commonly requires implantation of a neurostimulator, which, when activated, applies or delivers a stimulation signal to the vagus nerve of a patient. A vagus nerve stimulation signal is typically a periodic current pulse signal defined by an output current amplitude or intensity. In some VNS therapy systems, an external programming controller wirelessly communicates with the implanted device to control or alter one or more of the signal parameters.

Following implantation and activation of the neurostimulator, a full therapeutic dose of VNS is not immediately delivered to the patient to avoid causing significant patient discomfort and other undesirable side effects. Instead, to allow the patient to adjust to the VNS therapy, a titration process is utilized in which the intensity is gradually increased over a period of time under the control of a physician, with the patient given time between successive increases in VNS therapy intensity to adapt to the new intensity. As stimulation is chronically applied at each new intensity level, the patient's side effect threshold gradually increases, allowing for an increase in intensity during subsequent titration sessions.

SUMMARY

Embodiments of systems and methods are provided for monitoring physiological response to neurostimulation therapy. One embodiment relates to an assessment system for vagus nerve stimulation therapy treatment for congestive heart failure in a subject patient implanted with an implantable neurostimulator configured to deliver a periodic stimulation signal having a plurality of ON-periods and OFF-periods. Each ON-period is defined as time between an initiating pulse and a terminating pulse of a plurality of stimulation pulses delivered to the subject, and each OFF-period is defined as time between consecutive ON-periods. The assessment system includes a wand assembly configured to generate a delivery detection signal indicating delivery of an initiating pulse from the neurostimulator to the subject patient. The assessment system also includes a processor and a non-transitory computer-readable memory associated with the wand. The memory stores instructions that, when executed by the processor, cause the assessment system to record an ECG signal of the subject patient over at least one successive pair of ON- and OFF-periods and determine changes in heart rate dynamics to indicate autonomic response to the vagus nerve stimulation. The wand assembly includes a programming device configured to wirelessly communicate with the neurostimulator and a cable connector configured to form a surface contact with the programming device. The cable connector includes a detection circuit configured to indirectly detect a time of the initiating pulse to synchronize recording of the ECG signal with the initiating pulse.

Another embodiment relates to a method of assessing vagus nerve stimulation for congestive heart failure in a subject patient. The method includes detecting delivery of a stimulation signal from an implantable neurostimulator device in the subject patient with a wand assembly in communication with the neurostimulator and synchronizing a start of a recording of an ECG response signal with the stimulation signal delivery based upon the detection by the wand assembly.

BRIEF DESCRIPTION OF THE DRAWINGS

The accompanying drawings, which are incorporated herein and constitute part of this specification, illustrate exemplary embodiments of the systems and methods described herein, and together, with the general description given above and the detailed description given below, serve to explain the features of the systems and methods described herein.

FIGS. 6A-6B are views of a wand and cable connector assembly for use in the system of FIG. 4, according to exemplary embodiments.

FIG. 6C is a perspective view of a cable connector for use in the assembly of FIGS. 6A and 6B, according to exemplary embodiments.

FIG. 8B is an illustrative embodiment of an ECG response signal to the stimulation signal of FIG. 8A.

DETAILED DESCRIPTION

A titration process for VNS stimulation can take up to 10-12 weeks before a full therapeutic dosage can even be tolerated. In order to reduce or minimize the titration process time to a full therapeutic dose, it is desirable to monitor the physiological response to evaluate whether the applied stimulus dosage in the titration process is effective without inducing undesirable side effects. When delivering neurostimulation therapies to patients, it is generally desirable to avoid stimulation intensities that result in either excessive tachycardia or excessive bradycardia side effects. Accordingly, the neurostimulator may be adjusted to deliver varying stimulation intensities to the patient. To find a beneficial therapeutic level of neurostimulation, researchers have utilized the patient's heart rate changes. Accordingly, there remains a need for systems and methods for assessing a physiological response to the delivery of a vagus nerve stimulation signal. Moreover, there is a need to monitor the physiological response in synchronized manner with the stimulation signal so as to properly correlate the physiological response to the parameters of the stimulation signal. Additionally, there remains a need for systems and methods for synchronizing monitoring of stimulation and ECG signals in an indirect manner without accessing the internal controls or circuitry of the neurostimulator or its external controller.

Figure 1:
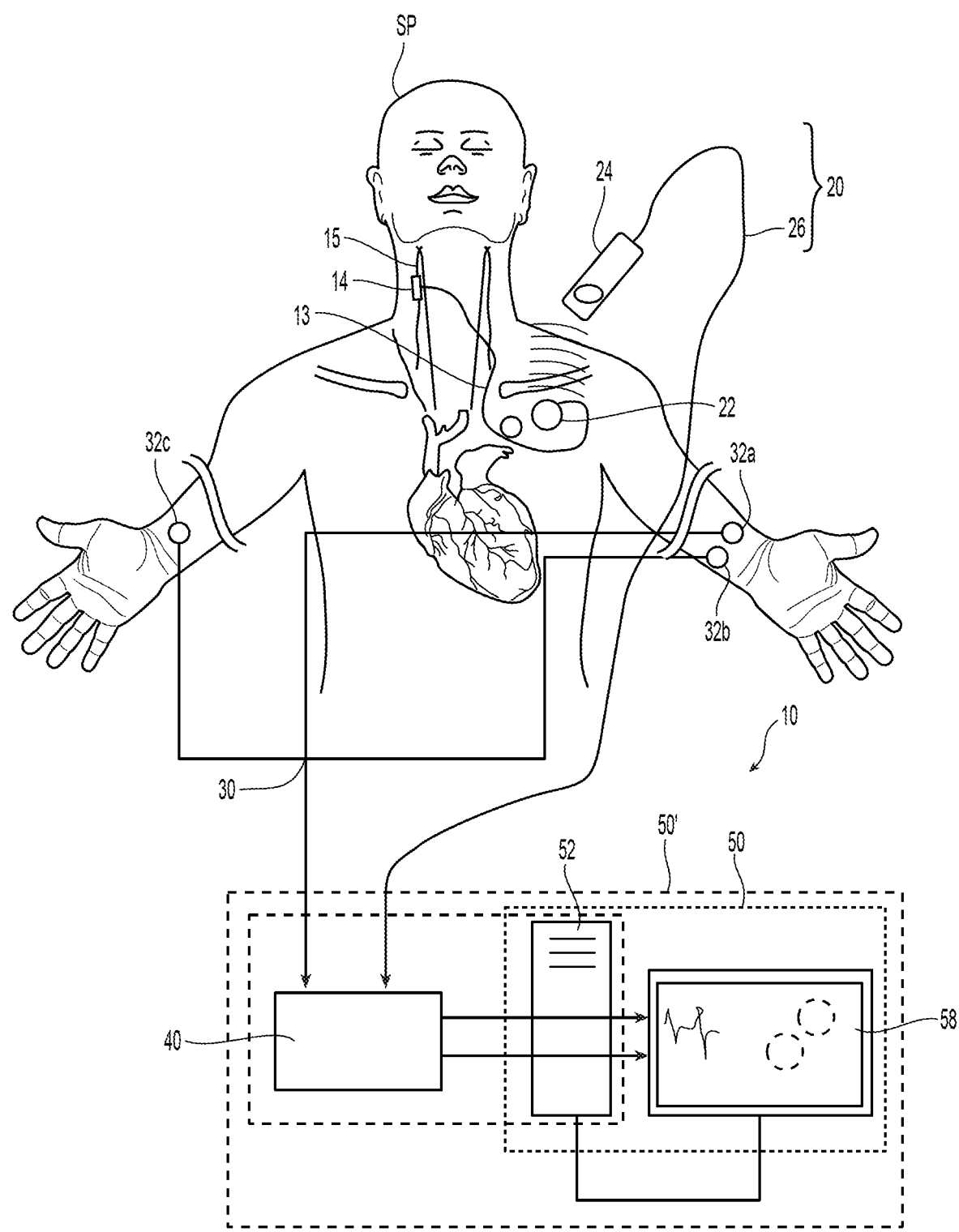
FIG. 1 a schematic view of a system for assessing vagus nerve stimulation for treatment of congestive heart failure, according to an exemplary embodiment.

Shown in FIG. 1 is a system 10 for monitoring and assessing a physiological response of a subject patient SP to neurostimulation therapy and, in particular, for monitoring and assessing heart rate dynamic response to vagus nerve stimulation for the treatment of CHF, according to an exemplary embodiment. In various embodiments, the system 10 captures the physiological response to the vagus nerve stimulation. In some embodiments, the system 10 (i) detects the electrical heart activity response, e.g., electrocardiogram ("ECG") of a subject patient in response to the vagus nerve stimulation signal from an implanted neurostimulator device; (ii) determines the change in heart rate dynamics in response to the stimulation; and (iii) visually displays the change in heart rate dynamics in a manner that indicates the extent of autonomic engagement in response to the delivered stimulus. The system 10 operates in a manner to indirectly detect the delivery of a stimulation signal from the implanted device for synchronized capture and recordation of the ECG signal.

The system 10 includes a first interface or communication assembly 20 for communication with a stimulation delivery device 22 and a second interface assembly 30 for capturing the physiological response of the subject patient SP. In some embodiments, the second interface assembly 30 captures data suitable for generating the ECG waveform of the subject patient SP to the stimulation delivery. Additionally, in some embodiments, the communication assembly 20 includes an external programming wand 24 and a wand transmission detection cable 26 to provide a communication assembly as described herein. The stimulation delivery device 22 is embodied as an implantable medical device ("IMD") and, more particularly, an implantable neurostimulator 22. Embodiments of the neurostimulator 22 are shown and described in U.S. Pat. Nos. 9,770,599 and 9,950,169, each of which is incorporated by reference in its entirety. As described in the cited patent documents, the implantable medical device includes a pulse generator 22, a lead 13, and electrodes 14 for delivering a pulse generated stimulus about a vagus nerve 15 of the subject patient SP. A commercially available embodiment of the implantable neurostimulator 22 includes the VITARIA™ Model 7103 Pulse Generator from LivaNova USA, Inc. of Houston, Tex., USA.

Figure 1A:
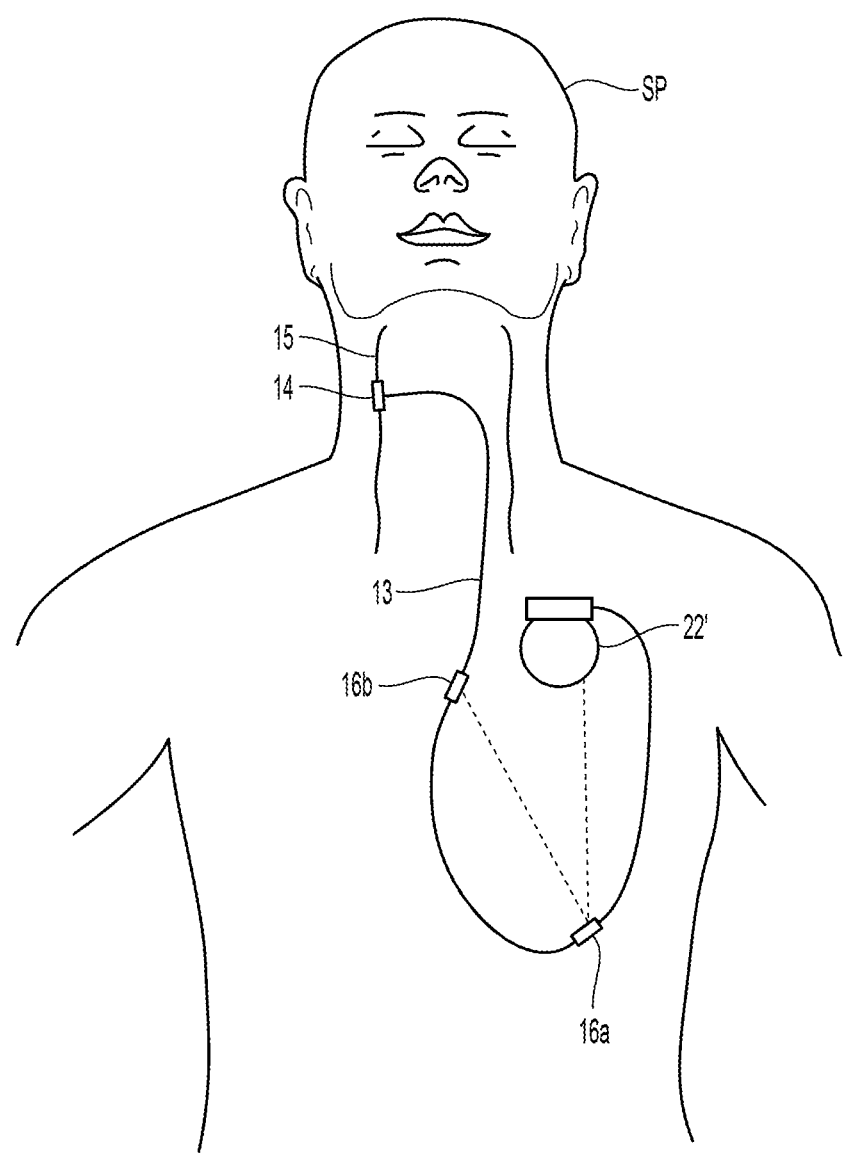
FIG. 1A is another schematic view of a neurostimulator for use in the system of FIG. 1, according to an exemplary embodiment.

Shown in FIG. 1A is another embodiment of a neurostimulator 22', for use with the assessment system 10, which includes or incorporates an implantable cardioverter-defibrillator ("ICD"). An implantable VNS/ICD system is also shown and described in U.S. Pat. No. 9,770,599, which is incorporated by reference in its entirety. An embodiment of an implantable VNS/ICD system includes a pulse generation module with a control system, a VNS subsystem, and an ICD subsystem. A first electrode assembly 14 is coupled to the pulse generation module and includes a VNS electrode configured to couple to the vagus nerve 15. A second electrode assembly 16a, 16b is coupled to the pulse generation module and includes a subcutaneous electrode. Another embodiment of an implantable VNS/ICD system includes a primary pulse generation module having a primary control system and an ICD subsystem and a secondary pulse generation module having a secondary control system and a VNS subsystem. The secondary pulse generation module is placed in data communication with the primary pulse generation module, with the second electrode assembly 16a, 16b coupled to the primary pulse generation module, in which the second electrode assembly 16a, 16b includes a subcutaneous electrode. Another electrode assembly is coupled to the secondary pulse generation module. This electrode assembly includes a VNS electrode 14 configured to couple to the vagus nerve 15. In various embodiments, the implantable VNS/ICD system is configured to deliver a chronic VNS therapy to the vagus nerve with a VNS subsystem of a pulse generation module. In response to detection of a cardiac event, deliver electrical cardioversion-defibrillation energy with an implantable cardioverter-defibrillator (ICD) subsystem of the pulse generation module.

Referring back to FIG. 1, a computer processing device 50 is coupled with the first and second interfaces 20, 30 for processing the captured ECG-suitable signal to determine, for example, in real-time, the heart rate dynamics in the subject patient SP in response to delivery of the stimulation signal to the vagus nerve. In some embodiments, the second interface assembly 30 is embodied as an ECG cable assembly with three leads or clips 32a, 32b, 32c for respectively connecting to three electrodes or contacts, for example, placed on the wrists of the subject patient SP. As seen in FIG. 1, two leads 32a, 32b are connected to two electrodes on the left wrist, and the remaining lead 32c is connected to a single electrode on the patient's right wrist. From the heart rate dynamics, the computer processing device 50 displays in real-time an indication of autonomic engagement in the subject patient SP in response to the stimulus.

The ECG-suitable signal allows the determination and display of a periodic waveform with repeating "cardiac cycles" as shown, for example, in FIG. 8B. A "cardiac cycle" may refer to one complete PQRSTU interval of the patient's heart functioning, ending with the P wave of the next succeeding cardiac cycle. An "interbeat interval" may refer to the time period between a predetermined point in a first cardiac cycle of the patient and the same predetermined point in the immediately succeeding cardiac cycle of the patient. Examples of interbeat intervals include an R-R interval, a P-P interval, or a T-T interval. Interbeat intervals may include a single interval or a moving average (either simple or weighted) of several consecutive intervals. Within a single cardiac cycle, a "cardiac period" is a length of time between a first point in the cardiac cycle of the patient and a second, later point. An exemplary cardiac period includes a P-wave, a Q-wave, an R-wave, an S-wave, a QRS complex, a T-wave, and a U-wave of the cardiac cycle, which can be readily identified by electrocardiography or other techniques of monitoring the electrical activity of the heart. For example, the R-wave presents the maximum amplitude of the cardiac cycle.

Figure 2:
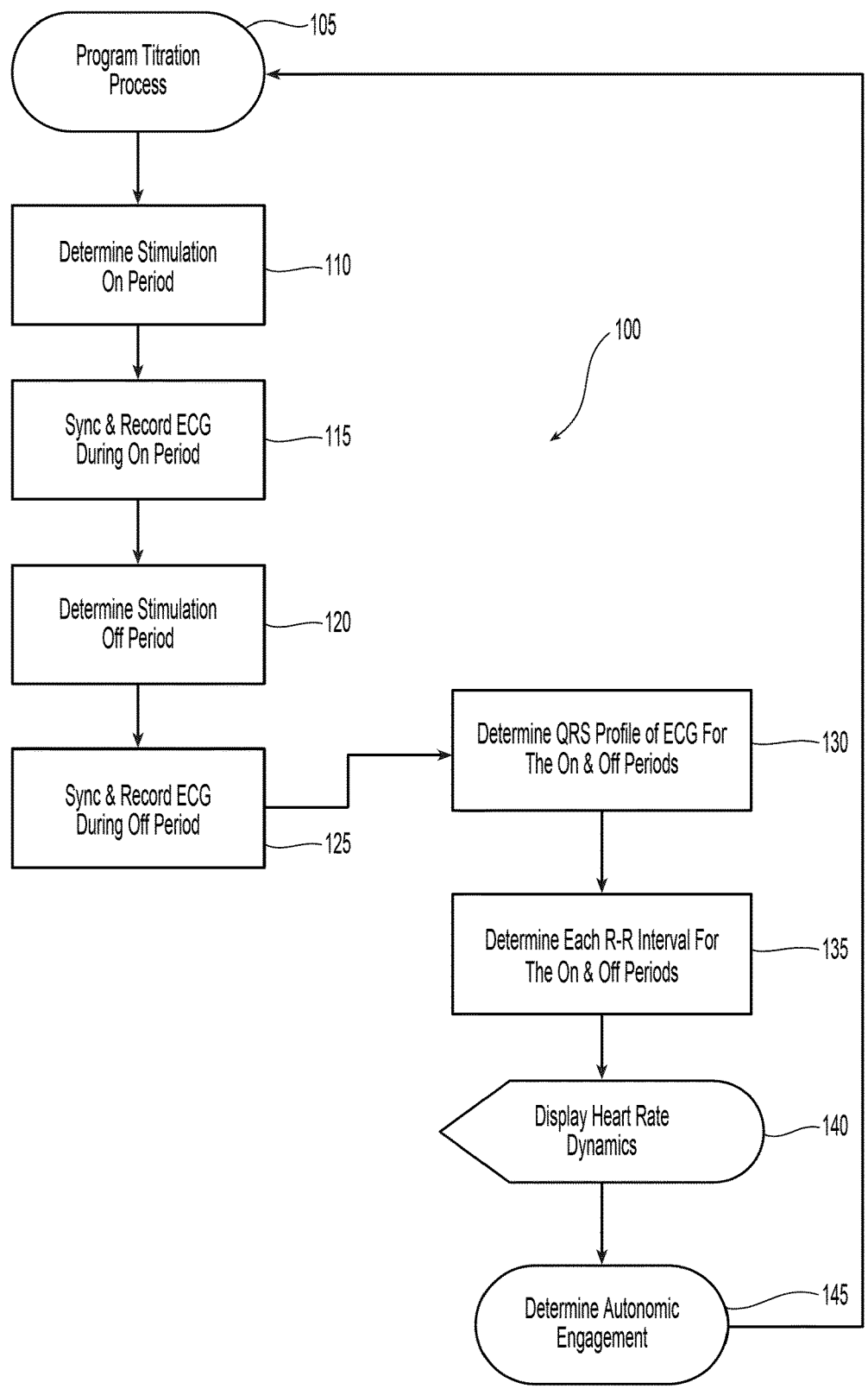
FIG. 2 is a method of assessment using the system of FIG. 1, according to an exemplary embodiment.
Figure 8A:
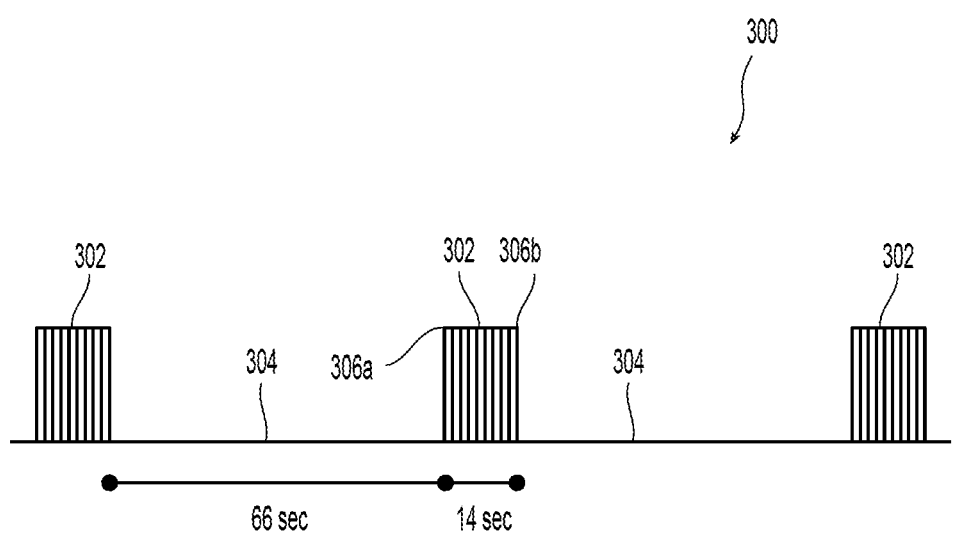
FIG. 8A is an illustrative embodiment of a stimulation signal.

Shown in FIG. 2 is a process 100 for capturing and analyzing the ECG signal response during vagus nerve stimulation treatment, according to an exemplary embodiment. At the beginning 105 of the titration or stimulation delivery process (e.g., as part of programming the titration process), a first determination step 110 is taken to determine when a stimulus signal is to be delivered from the neurostimulator 22 to the vagus nerve. In some embodiments, the stimulation signal is periodic having an ON-period in which stimulation of a particular current amplitude and frequency is delivered and an OFF-period of rest in which no stimulation signal is delivered to the vagus nerve. Shown in FIG. 8A is an exemplary stimulus signal 300 defined by one or more of the following parameters: output current amplitude or intensity, signal frequency, or pulse width. The vagus stimulation signal 300 is delivered in a cyclical manner in which each cycle of is defined by an ON-period 302 in which the stimulation signal is delivered to the vagus nerve and an OFF-period or rest period 304 in which no stimulation is delivered. Referring back to FIG. 2, with the schedule of ON-periods determined, the process 100 includes a synchronization and recordation step 115 in which an ECG-suitable signal is captured and recorded over the ON-period. In a second determination step 120, the OFF-period of the stimulation signal is identified. In some embodiments, the OFF-period is continuous with the ON-period and is identifiable as being the rest period between two adjacent ON-periods in the stimulation signal. With the OFF-period identified, a second synchronization and recordation step 125 is carried out to capture and record the ECG-suitable signal. Although FIG. 2 shows the determination and recordation steps as discrete steps, the steps may be carried out sequentially, concurrently, or in an alternate order.

Having captured and identified the ECG-suitable signals in a synchronized manner with the ON- and OFF-periods of the stimulation signal, the heart rate dynamic response corresponding to each of the ON-period and OFF-period in the stimulation signal can be determined to assess the autonomic engagement response to the stimulation treatment. As such, in the assessment method 100, a third determination step 130 is carried out to determine the QRS complex profile in the corresponding ECG waveforms for each period of the stimulation signal. A fourth determination step 135 includes determining each R-R interval between consecutive QRS complexes in each ECG-suitable signal corresponding to the ON-period and OFF-period in the stimulation signal. Accordingly, heart rate dynamic response, such as, for example, instantaneous heart rate, mean heart rate, and heart rate variability, can be determined and displayed in a subsequent step 140 for each of the ON-period and OFF-period in the stimulation signal. The process 100 can then conclude with an assessment step 145 in which the autonomic engagement response can be determined, indicated, and displayed for the subject patient and/or clinician.

Figure 3:
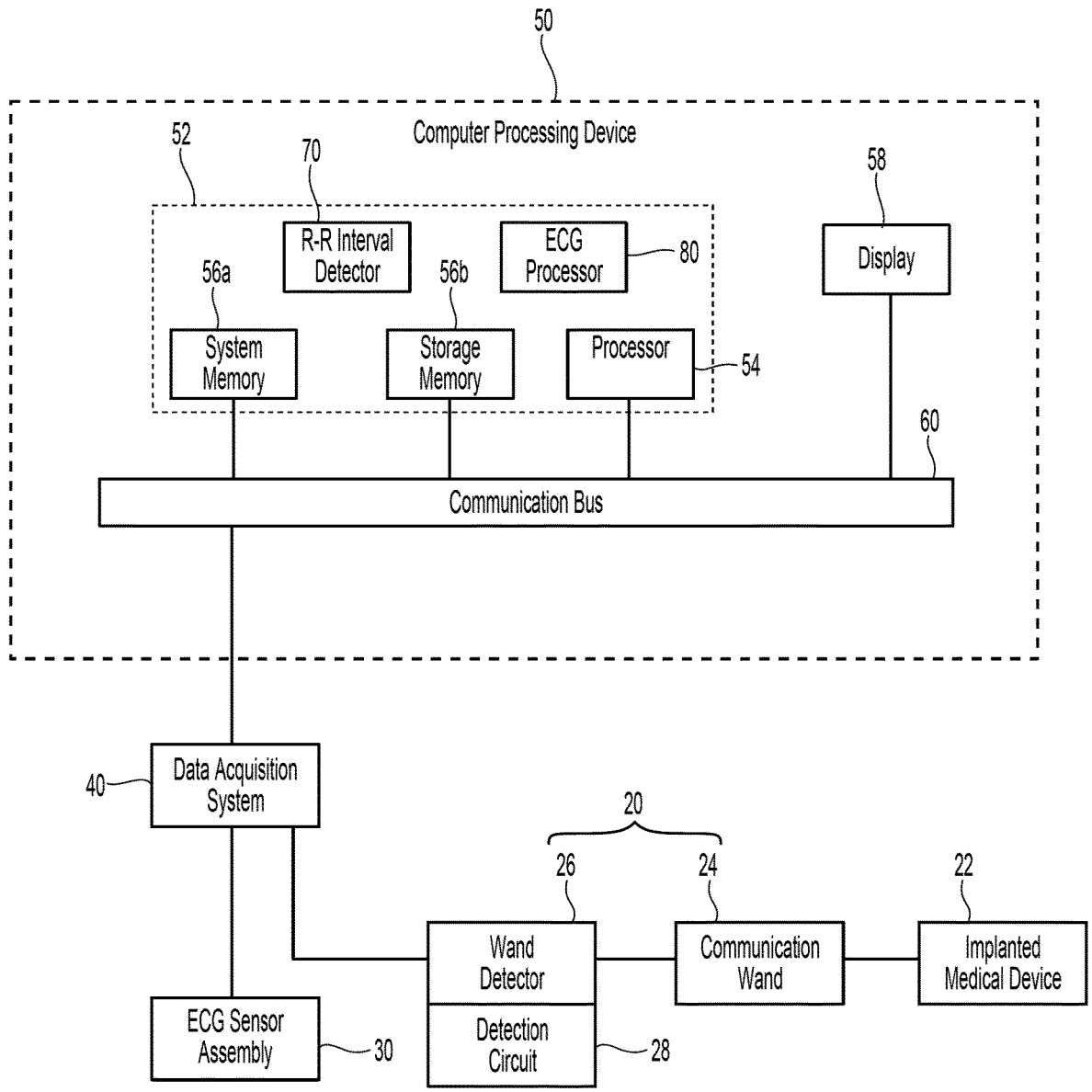
FIG. 3 is a schematic view of an embodiment of the system of FIG. 1.

Shown in FIG. 3 is another schematic view of the system 10 that synchronizes stimulation delivery and the ECG-suitable signal monitoring for assessing the vagus nerve stimulation treatment. In the system 10, the communication assembly 20 wirelessly communicates with the neurostimulator 22 by providing control signals or commands to define parameters of the stimulation signal or pulses to be delivered by the neurostimulator 22 to the vagus nerve. In some embodiments, the communication assembly 20 is embodied as a wand assembly 20 that includes a programming device or wand 24 and a wand transmission detection cable 26. The programming wand 24 is a hand-held device that operates externally to the implanted device 22 and wirelessly communicates with the device 22 by telemetry or radio frequency signal. Embodiments of the external programming wand 24 are described, for example, in U.S. Pat. Nos. 9,770,599 and 9,950,169. A commercially available embodiment of the wand 24 includes NeuroCybernetic Prosthesis (NCP®) Programming Wand Model 201. The wand 24 can wirelessly transmit programming and interrogation information signals or commands to the implantable neurostimulator 22, such as, for example, the VITARIA™ Model 7103 Pulse Generator. The programming wand 24 has an outer casing that houses an internal computer processor for executing appropriate firmware, such as, for example VNS Therapy Programming Software, that can store and retrieve telemetry data and revise stimulus signal parameters from the pulse generator 22.

The wand transmission detection cable 26 is associated with the external programmer or wand 24 to detect or determine the stimulation delivery from the neurostimulator 22 to the vagus nerve 15 of the subject patient SP. In some embodiments, the detection cable 26, by an indirect device or mechanism that includes a detection circuit 28, detects or extracts the delivery or delivery schedule from the external wand 24 to determine the stimulation delivery from the neurostimulator 22 to the vagus nerve. By detecting delivery of the stimulation signal with the communication assembly 20, the capture or recordation of the subject's ECG-suitable signal can be synchronized with the ON-period and OFF-period of the stimulation signal in accordance with the process 100 for capturing and analyzing the ECG-suitable signal in a manner as previously described.

Figure 4:
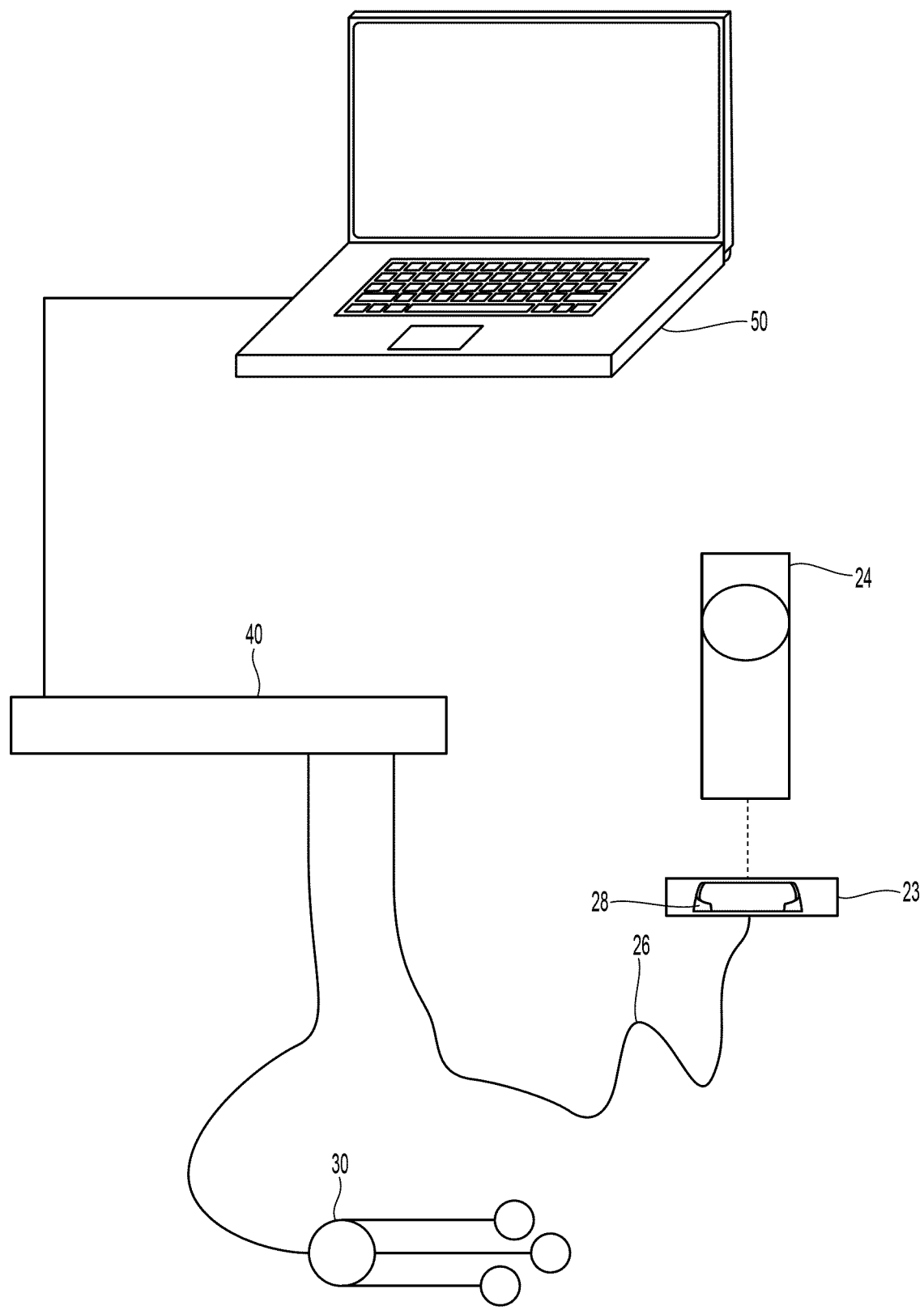
FIG. 4 is a schematic view of an embodiment of the system of FIG. 3.

Shown in FIG. 4 is an exploded schematic view of the system 10, according to an exemplary embodiment. The wand detection assembly includes a cable connector 23 for engaging the wand 24 and its outer casing to form a surface contact. In some embodiments, the cable connector 23 forms a close-fit or mechanical latch about the wand 24. With the cable connector 23 disposed about the wand 24, the detection circuit 28 of the wand transmission detection cable 26 is able to indirectly detect the stimulation signal delivery or the schedule thereof from the implantable medical neurostimulator device 22 when the wand 24 is placed in communication with the neurostimulator 22. Because the wand detection cable 26 does not directly access the internal processor or circuitry of either the wand 24 or the neurostimulator 22, the wand detection cable 26 indirectly detects the stimulation signal delivery to the vagus nerve.

Figure 5:
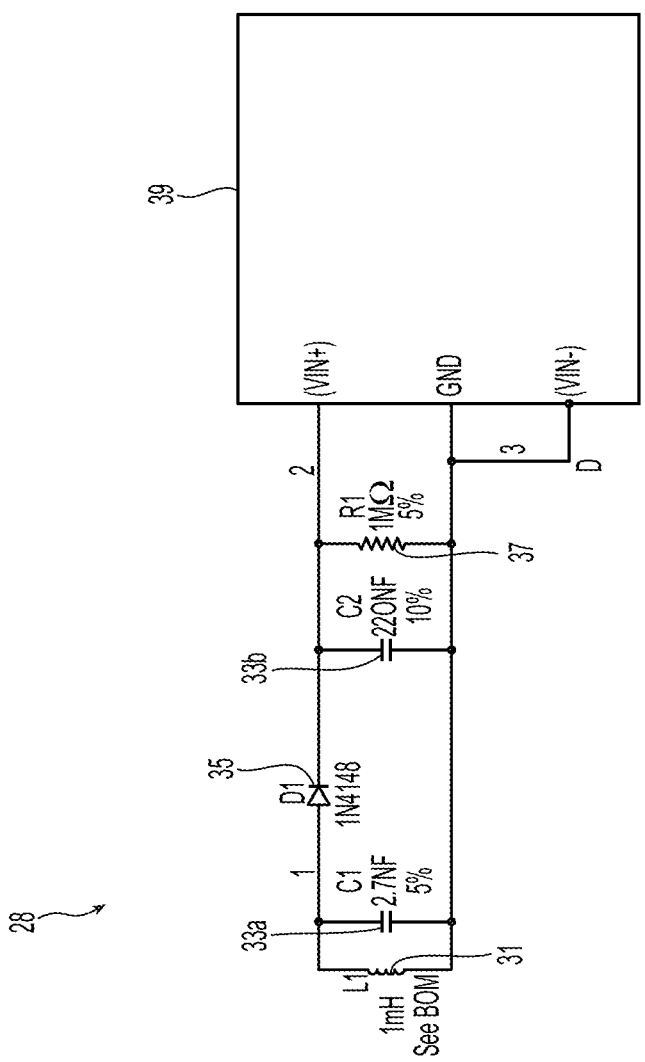
FIG. 5 is a schematic of a detection circuit for use in the system of FIG. 4, according to an exemplary embodiment.

Shown in FIG. 5 is an embodiment of the detection circuit 28. The detection circuit 28 includes an inductor 31 and a parallel capacitor 33$a$ to detect, by induction and resonance, wand transmission from the wand 24 that is indicative of stimulation signal delivery from the neurostimulator 22. Additionally, the detection circuit 28 includes a diode 35 and parallel capacitor 33$b$ and resistor 37, providing a diode rectifier and RC low pass filter to detect wand transmissions. The detection circuit 28 is connected to a three lead convolution or yoke 39 defining the positive lead VN+, a negative lead VN−, and a ground lead GND. The lead yoke 39 forms one end of the cable assembly 20 from which a cable carrying the three leads extends for signal input to the computer processing device 50.

In transmission, the wand 24 is placed in communication with the neurostimulator 22, where the neurostimulator 22 is configured to provide inductive telemetry transmission to indicate stimulation signal delivery to the vagus nerve 15. The wand transmission induces an AC voltage across the inductor 31 and first capacitor 33a. The diode 35 rectifies the AC voltage, which is then filtered by the second capacitor 33b and resistor 37. In some embodiments of the detection circuit 28, the RC low pass filter formed from the parallel capacitor 33b and resistor 37 can define a threshold for which the induced voltage is to exceed to define a stimulation signal delivery. The output voltage across the circuit 28 can then be used by the computer processing device 50 to derive and then indicate stimulation signal delivery.

Shown in FIG. 6C is an embodiment of the cable connector 23 that engages the wand 24 and houses the detection circuit 28. The cable connector 23 includes a pair of spaced arms 23a, 23b with a circuit housing 25. The arms 23a, 23b can flex with respect to the housing body 25 to resiliently accommodate insertion of the wand 24 to form the mechanical latch about the wand 24 as shown in FIGS. 6A and 6B, according to exemplary embodiments. The detection circuit 28 is secured within the housing 25 by, for example, an appropriate potting and hot glue encapsulation.

Referring again to FIG. 3, the computer processing device 50 includes processing hardware 52, such as, for example, a central processing unit 54 and associated memory or computer readable medium, such as, for example, system memory 56a and storage memory 56b, for processing ECG-suitable signals in a manner as described herein. The system memory 56a can include volatile memory, such as, for example, RAM (random-access memory). The storage memory 56b can be non-volatile or persistent memory such as for example, ROM (read-only memory), flash memory, ferroelectric RAM, most types of magnetic computer storage devices (e.g. hard disk drives, solid state drives, floppy disks, and magnetic tape), or optical discs. The computer processing device 50 includes one or more associated displays 58 for indicating the autonomic engagement response to the stimulus. The system memory 56a and/or storage memory 56b may store instructions that are executable by the processor 54 to perform the functionalities described herein. The display 58 can be a touch-sensitive display, which can provide touch control buttons and keys. As shown, the processing hardware 52 and the display 58 communicate with one another over a communication bus or network 60. Additionally or alternatively, the computer processing device 50 can include one or more peripheral input and output ports for connection and use with other peripheral input, output, or storage devices. The components of the computer processing device 50 can be integrated with one another or be separately housed components. For example, the processing hardware 52 can be housed separately from the display 58. Alternatively, the display 58 can be housed with the processing hardware 52 in a single assembly. In some embodiments, the computer processing device 50 can be embodied using a general purpose programmable computer. A general purpose programmable computer can be a personal computer, laptop computer, Ultrabook computer, netbook computer, handheld computer, tablet computer, smart phone, or other form of computational device with an appropriate operating system. In other embodiments, the computer processing device 50 can be a specialized computer specifically designed and programmed to functions with the neurostimulator 22 described herein.

In the system 10, the computer processing device 50 is coupled to each of the first and second interface communication assemblies 20, 30 by a data acquisition system 40. The data acquisition system 40 provides for digital conversion of incoming analog signals coming from the interface communication assemblies 20, 30 (e.g., a wand assembly 20, ECG sensor assembly 30). As shown, the data acquisition system 40, the processing hardware 52, and the display 58 communicate with one another over the communication bus or network 60. In some embodiments, the data acquisition system 40 for use in the system 10 is the BIOPAC MP36R from BIOPAC® Systems, Inc., which can simultaneously capture signals from multiple devices or sources. Additionally, in some embodiments, the computer processing device and the data acquisition system are different systems (e.g., shown as computer processing device 50 and data acquisition system 40 in FIG. 1), while in other embodiments, the computer processing device and data acquisition system are incorporated into a single system (e.g., shown as computer processing device 50' in FIG. 1).

The computer processing device 50 operates under the control of one or more software applications, which are executed as program code as a series of process or method modules or steps by the programmed computer hardware. In some embodiments, a computer readable medium, such as a non-transitory computer readable medium, of the processing hardware 52 stores a program that can cause the computer processing device 50 to execute one or more processes described herein for synchronizing the ECG recording with the stimulation signal and assessing vagus nerve stimulation treatment.

In the embodiment of the system 10 and its operation 100 of FIG. 2, the system 10 processes the ECG-suitable signal response to determine heart rate dynamics. Moreover, the system 10 distinguishes or identifies which portions of the ECG signal or waveform response correspond to the delivery of stimulation signal, i.e., the ON-periods of the periodic stimulation signal, and which portions of the ECG signal or waveform response correspond to the rest period, i.e., the OFF-periods of the periodic stimulation signal. By segregating ECG signals or portions of the ECG waveform and their derivative components by ON-period and OFF-period, the ECG signals/waveforms and the heart rate dynamics derived therefrom can be compared to assess the extent of autonomic engagement resulting in the delivered stimulation signal.

Referring again to FIG. 3, the computer processing device 50 and its hardware includes and executes firmware programming that provides for an R-R interval detector 70 and an ECG processor 80 for carrying out the assessment methods described herein. The R-R interval detector 70 and ECG processor 80 and the associated methods can be implemented using appropriate software programming for signal processing and hardware configuration. For example, an appropriate "graphical program" can be used to represent data structures and/or program instructions in memory (e.g., the system memory 56a and/or storage memory 56b) of the computer processing device 50 to carry out the signal processing, instrument access, and assessment methods described herein. An exemplary graphical program development environment in which to create a program for use in the system 10 includes LabVIEW from National Instruments Corp.

Figure 7A:
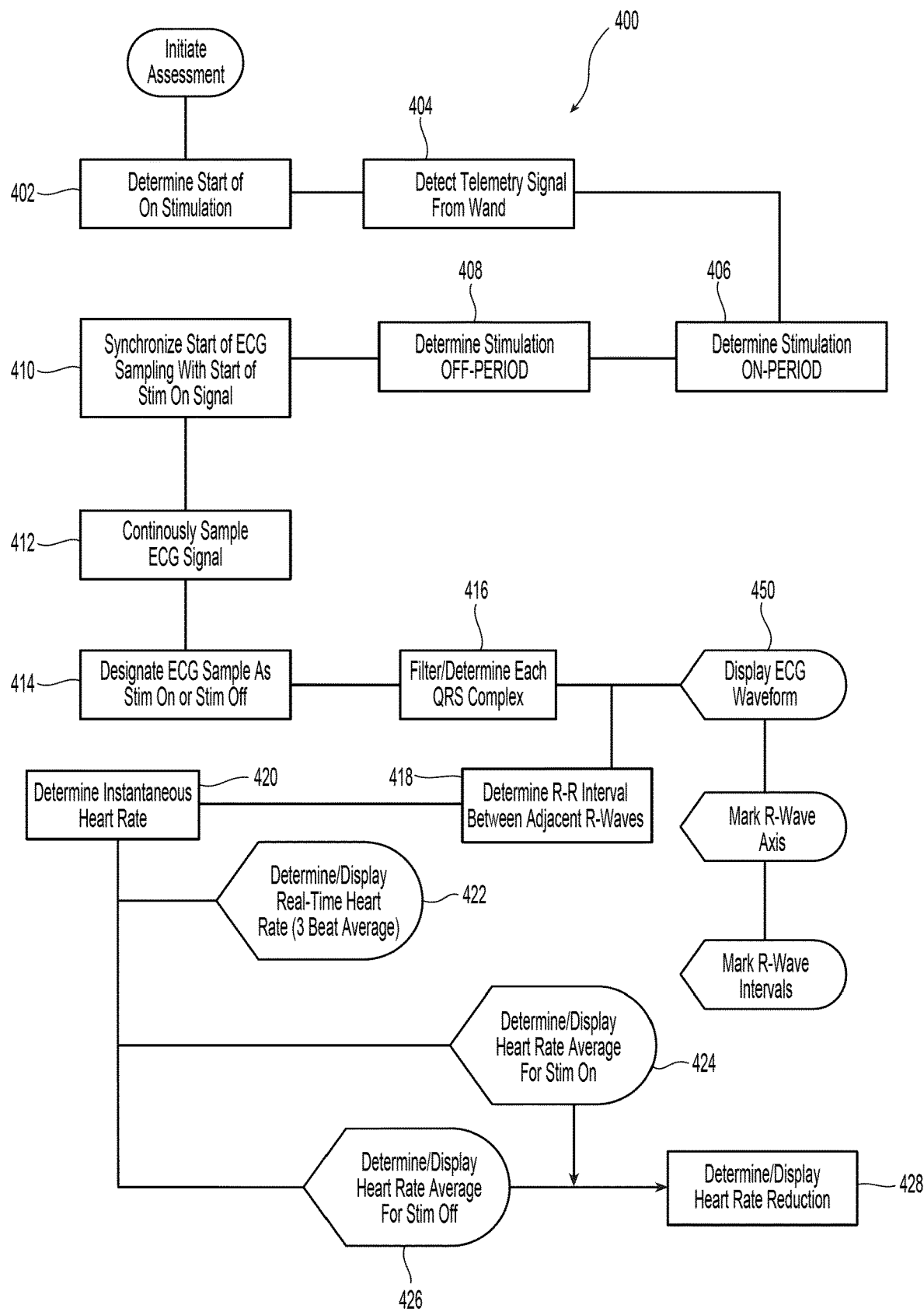
FIGS. 7A and 7B are embodiments of methods of assessment using the system of FIG. 4, according to exemplary embodiments.

Shown in FIG. 7A is an embodiment of the assessment process 400. With the subject patient SP connected to the system 10, as shown in FIG. 1, and the implanted neurostimulator medical device 22 delivering a stimulation signal to the vagus nerve of the patient, the process of assessment 400 begins with a determination step 402 to determine the start of stimulation delivery for synchronizing recordation of the cardiac response. In some embodiments, the programming wand 24 is placed in communication with the neurostimulator 22, and the wand transmission detection cable 26 in combination with the computer processing device 50 detects the inductive telemetry signal between the components (step 404). For example, the wand 24 emits a series of energy or inductive telemetry transmissions to program the neurostimulator 22. The wand transmission detection cable 26 and its detection circuit 28 detect the last burst that corresponds to a start of a stimulation signal cycle. The wand transmission detection cable 26 communicates the detection to the computer processing device 50, which can determine the delivery sequence (e.g., the ON-period and OFF-period) of the stimulation signal.

Referring again to FIG. 8A, the ON-period 302 occurs at a constant interval with the OFF-periods 304 of rest between the repeating ON-periods 302. In some embodiments, a treatment cycle can be defined by a combination of on and off times selected from the following exemplary ON-periods: 7 sec, 14 sec, 21 sec, 30 sec, 50 sec, and 60 sec; and exemplary OFF-periods: 12 sec, 18 sec, 24 sec, 30 sec, 42 sec, 54 sec, 66 sec, 78 sec, 90 sec, 120 sec, 180 sec, and 300 sec. For example, one exemplary treatment cycle is defined by a 14 second ON-period and a 66 second OFF-period. A cycle of stimulation delivery is defined by a continuous series of ON-periods 302 and OFF-periods 304. In one treatment, there are 5-10 cycles.

Each ON-period 302 is defined by repeating pulse signals at a defined output current amplitude or intensity, signal frequency, and pulse width. In one exemplary ON-period 302, the pulse signals are defined by an output current of up to 3.0 mA, a frequency of 5-10 Hz, and a pulse width at 250-300 micro-seconds ("μsec"). Accordingly, each ON-period 302 is defined by an initiating pulse 306a and a terminating pulse 306b that are spaced apart over a time duration defining the ON-period 302. The OFF-period 304 is thus defined by the time duration between a terminating pulse 306b of one ON-period 302 and the initiating pulse 306a of the subsequent ON-period 302. Although the stimulation signal is shown as a square pulse, the signal can alternatively include a ramp up period to the initiating pulse 306a and a ramp down period from the terminating pulse 306b.

Referring again to FIG. 3 and FIG. 7A, the computer processing device 50 determines the stimulation ON-period (step 406) and determines the stimulation OFF-period (step 408) from the detection signal from the wand transmission detection cable 26. The computer processing device 50 can also be provided with the stimulation parameters (e.g., via the wand 24 or via a user input). Once the wand transmission is detected by the cable 26, the computer processing device 50 can determine the start, duration, and termination of each of the ON-periods and OFF-periods. At step 410, the computer processing device 50 synchronizes sampling of the ECG-suitable signal with start of the ON-period of the delivered stimulation signal (e.g., such that the ECG-suitable signal is continuously recorded). With the start of ECG recording synchronized with the stimulation signal, the ECG response signal is continuously sampled at sampling step 412 by the data acquisition system 40 and the computer processing device 50. For example, the ECG-suitable signal is sampled at a rate of 200 samples per second at a rate suitable for analysis and processing as described herein.

In an exemplary ECG processing step 414, the digitally converted ECG-suitable signal is segregated and designated into portions that correspond to the ECG response to the ON-period of stimulation delivery and the ECG response to the resting OFF-period. The R-R interval detector 70 identifies portions of the incoming ECG response as corresponding to either the ON-period or the OFF-period of the stimulation signal to complete step 414 of FIG. 7A. Illustrated in FIG. 8B is a first portion 220 of the sampled ECG signal corresponding to the ON-period of the stimulation signal and a second portion 230 of the sampled ECG signal corresponding to the OFF-period of the stimulation signal.

Each of the designated portions 220, 230 of the ECG response is then processed to determine its waveform components for analysis and digital reconstruction. Indicated in FIG. 8B are QRS complexes for the ON-period ECG waveform portion 220 and QRS complexes for the OFF-period ECG waveform portion 230. FIG. 8B also includes R-R intervals (228 for the first portion 220, 238 for the second portion 230), or time periods between adjacent R-waves in the ECG waveform or equivalent ECG characterization. Accordingly, in various embodiments, the R-R interval detector 70 of FIG. 3 determines and verifies the R-R intervals to complete the determination and filter steps 416, 418 in the process 400 of FIG. 4. With each R-wave and R-R interval identified within the ECG waveform or equivalent, the computer processing device 50 determines one or more heart rate dynamics for assessment of the delivered stimulation signal.

Referring again to FIG. 3, the ECG processor 80 is configured to calculate and provide one or more of the following: a heart rate, a heart rate variability, and digital ECG waveform. In some embodiments, in accordance with step 420 of the process 400 of FIG. 7A, for each R-R interval, the instantaneous heart rate ("IHR") in beats per minute ("bpm") is determined by the following:

$$\text{IHR} = 1 \text{ beat}/(R\text{-}R \text{ interval msec}) \times (1000 \text{ msec/sec}) \times (60 \text{ sec/min})$$

From the IHR several statistical aspects of the heart rate can also be determined. In some embodiments, the real-time heart rate can be determined at step 422 by taking a beat-to-beat average over a range of the latest recorded number of beats. For example, the real-time heart rate ("RTHR") can be determined by the average of the last five or fewer instantaneous heart rates. As can be appreciated, the IHR values can be qualified values that meet a threshold level of data quality, with inaccurate or inconsistent IHR values being disregarded, discounted, weighted, or modified to improve the quality of the IHR values used in the determination of the RTHR value. As can also be appreciated, the IHR values can be ordered in time in a sequence with each value being adjacent to the next in time, ordered in time in a sequence with unqualified IHR values interposed between qualified IHR values, and/or ordered in time in a sequence with a skipped IHR value or values interposed between qualified IHR values.

In a continuous manner, the storage memory 56b, in coordination with the R-R interval detector 70, stores in one or more data arrays each IHR, associated verified R-R interval, associated status identifier as either ON-period or OFF-period, and associated cycle number in the number of cycles defining the stimulus treatment. The ECG processor 80 determines, in real-time, the mean heart rate for each ON-period of stimulation signal delivery and OFF-period of rest in a given treatment cycle in steps 424, 426 of the process 400. For example, where a stimulation signal cycle is defined by a 14 second ON-period and a 66 second OFF-period, the ECG processor takes the cumulative average of most or all the IHRs over the 14 second ON-period to determine the ON-period mean heart rate ("(MHR)ON"). To determine the OFF-period mean heart rate ("(MHR) OFF"), the ECG processor 80 takes the cumulative average of most or all IHRs over the 66 second OFF-period. In one embodiment, the IHR values corresponding to the ON-period and/or the OFF-period can be qualified to eliminate low-quality IHR values or to eliminate IHR values that overlap or are proximate to the start or cessation of stimulation.

In step 428 of process 400, the ECG processor 80 determines (e.g., in real-time) the extent of bradycardia response (e.g., a heart rate reduction response) for each cycle of treatment by determining the difference between the cumulative averages of the instantaneous heart rates to indicate a heart rate reduction ("HRR") as follows:

$$HRR=(MHR)OFF-(MHR)ON$$

A positive HRR indicates a bradycardia response, and a negative HRR indicates a tachycardia response. A positive HRR reduction of less than 5% from the mean heart rate for the OFF-period ((MHR)OFF) indicates a desired response of autonomic engagement (e.g., a response within the neural fulcrum zone). The HRR may also be displayed at step 428.

Figure 7B:
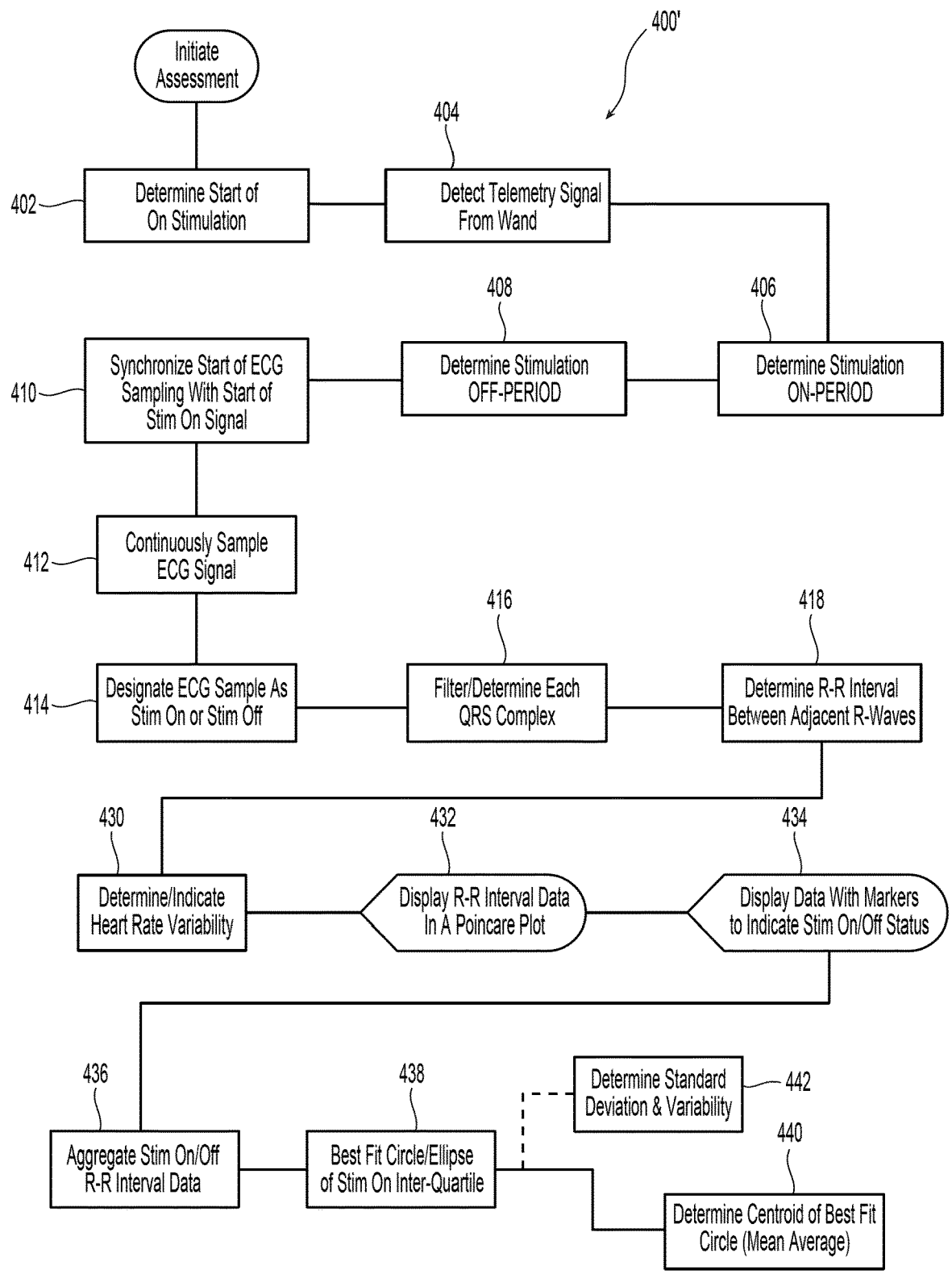

The ECG processor 80 is also configured to determine heart rate variability in step 430 of an additional or alternate method 400' for assessing response to the vagus nerve stimulation as shown in FIG. 7B. In particular, the ECG processor 80 determines a difference in the heart rate variability response between the ON-period and the OFF-period. In an aspect, the storage memory 56b, in coordination with the ECG processor 80, stores in one or more data arrays the R-R interval for each preceding R-R interval and stimulation status ON/OFF period for a number of cycles in the stimulation treatment. Accordingly, the stored data array can be defined as {R-R Interval(N+1), R-R Interval(N), ON/OFF-period Status, # Cycle}. The data can be aggregated for each cycle in a manner that differentiates ON-period of stimulation signal delivery and OFF-period of resting period. In some embodiments, for each cycle, the mean average of all the R-R Intervals for the ON-period and the mean average of all the R-R Intervals for the OFF-period are determined and compared. A separation in the mean average can be used to show an autonomic engagement response to the delivery of vagus nerve stimulation treatment.

Figure 9A:
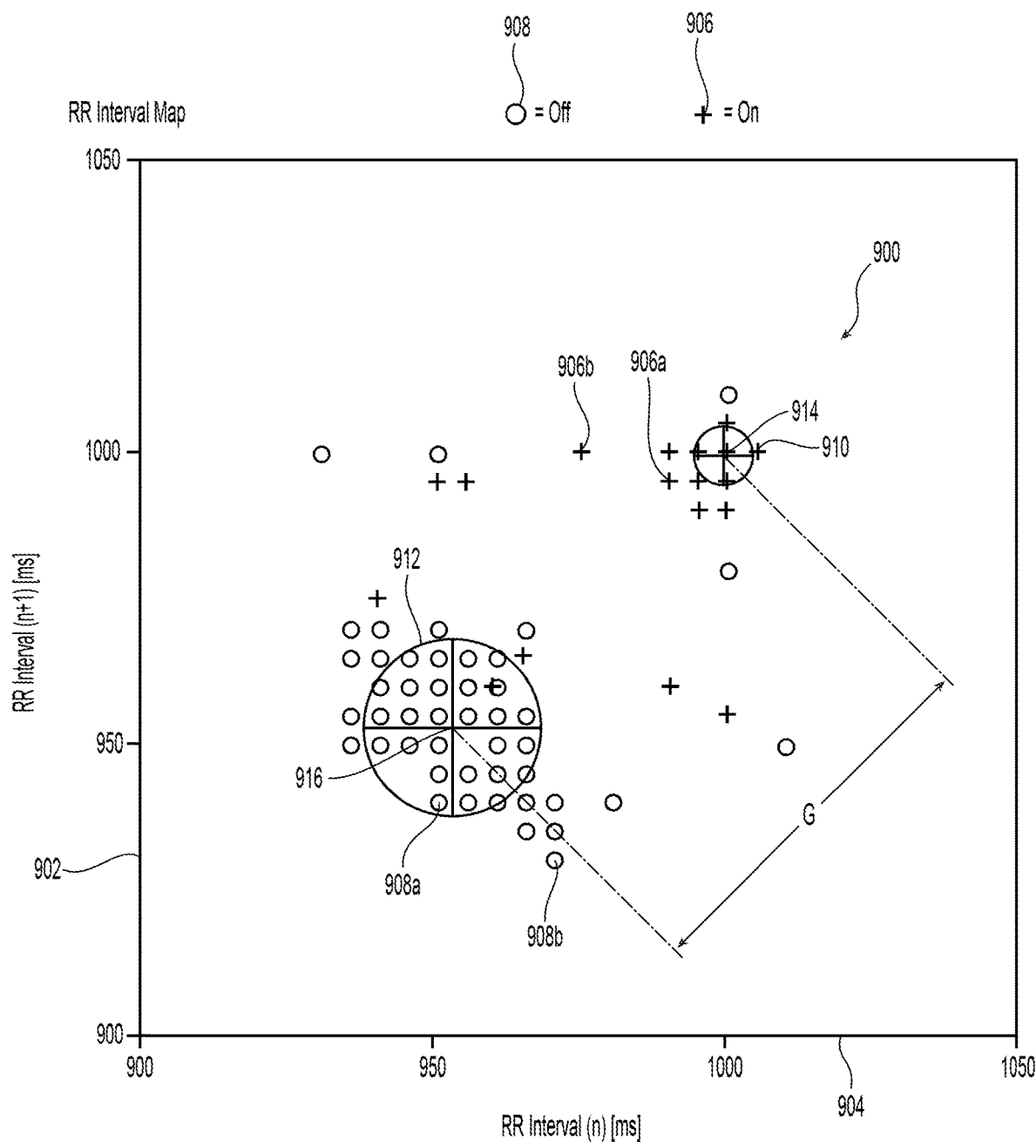
FIGS. 9A and 9B are illustrative assessments using the system of FIG. 4, according to exemplary embodiments.

In an aspect of the assessment method 400', the heart variability is graphically displayed in a display step 432 that provides the subject patient SP or clinician with a real-time indicator of autonomic engagement response to a delivered stimulus. More particularly, the R-R interval differential between the ON-period and OFF-period is displayed in a Poincaré plot 900 as illustrated in FIG. 9A. The display can be generated (e.g., in real-time) for the subject patient SP or clinician to view at the display 58 of the system 10. The plot shows the R-R interval (R-R Interval(N+1)) along the vertical axis 902, in msec, as a function of the preceding R-R interval (R-R Interval(N)) along the horizontal axis 904 in msec. In step 434 of the process 400', the R-R intervals are for the ON-period and OFF-period are distinguished from one another by differentiating markers. For example, R-R interval values for the ON-period are shown with "+" markers 906, and the OFF-period values are shown with "O" markers 908.

In accordance with an aggregating step 436 of the process 400', the plot 900 provides a visual indication of autonomic engagement as determined by the separation or gap G between the cluster of ON-period R-R interval values from the cluster of OFF-period R-R interval values. In another process step 438, the plot 900 shows a first best-fit circle 910 about the R-R interval ON-period data (e.g., 906a, 906b) and a second best-fit circle 912 about the R-R interval OFF-period data (e.g., 908a, 908b). The best-fit circles 910, 912 are defined by a radius about the centroids 914, 916, which are determined by the respective means of the ON-period and OFF-period R-R interval data at step 440. Alternatively, the data can be analyzed and aggregated about a best fit ellipse. Additionally, in some embodiments, the standard deviation and variability of the ON-period R-R interval values and OFF-period R-R interval values are determined at step 442 (e.g., as part of determining axes for the best-fit circles 910, 912).

Figure 9B:
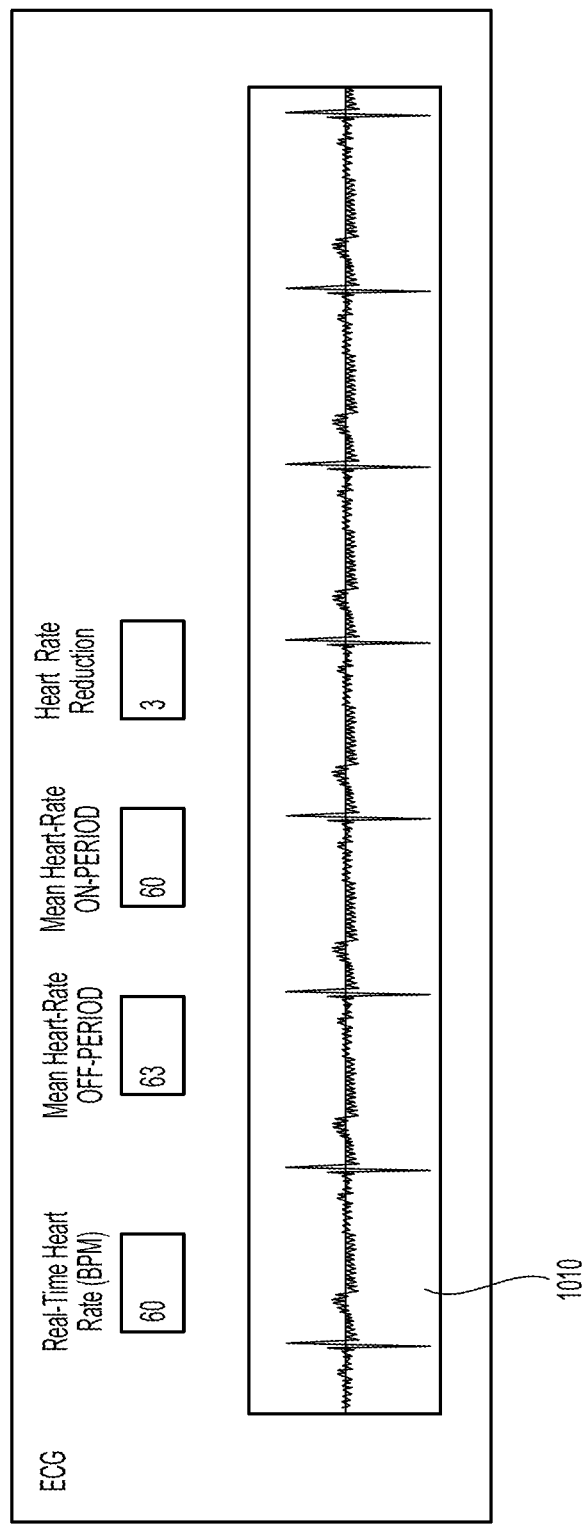

Given the data compiled and collected by the computer processing device 50, the ECG processor 80 can also, in step 450 of method 400 of FIG. 7A, generate and display a digital replica of the ECG waveform 1010 in the display 58 in real-time, as shown, for example, in FIG. 9B. The ECG replica 1010 includes all the PQRSTU intervals of the waveform to provide a visual indicator to the subject patient, clinician, and/or physician of any possible arrhythmia to accompany the assessment indicators previously described. Moreover, the display 58 can display back to the subject patient or clinician each of the determined values from the assessment processes previously described. For example, the display 58 can report back the real-time heart rate (RTHR), the mean heart rates for each of the OFF-Period and ON-Period ((MHR)OFF, (MHR)ON)), and the heart rate reduction (HRR). Additionally, in some embodiments, the display 58 can show the R-wave axis and/or mark the R-wave intervals for the subject patient or clinician.

As described herein, embodiments of the system 10 provide one or more indicators to a patient and/or clinician of the effectiveness of a delivered stimulation treatment by indicating autonomic engagement in the subject patient in a timeframe that is real-time, which includes a timeframe that is instantaneous, immediate, sequential or proximate to a parameter change; encompassing a titration session; and/or within one minute, ten minutes, and/or an hour of a stimulation parameter change. In some embodiments, the one or more real-time indicators of the effectiveness of a delivered stimulation treatment allow and/or facilitate the modification of the stimulation therapy, the subject patient's advancement through the titration process, and/or the delivery of effective levels of therapy to the subject patient in a timeframe that is real-time, which includes a timeframe that is instantaneous, immediate, sequential, or proximate to a parameter change; encompassing a titration session; and/or within one minute, ten minutes, and/or an hour of a stimulation parameter change. Alternatively or additionally, the titration process can be automatically altered or increased in intensity with the detection, monitoring, and/or measurement by the system 10 occurring in real-time. The assessment can be read from system 10 in real-time, or, if needed or desired, the assessment can be read from the system 10 by a clinician at a later time in a clinic or other environment.

For the purpose of this disclosure, the term "coupled" means the joining of two members directly or indirectly to one another. Such joining may be achieved with the two members or the two members and any additional intermediate members being integrally formed as a single unitary body with one another, or with the two members or the two members and any additional intermediate members being attached to one another. Such joining may be permanent in nature or may be removable or releasable in nature.

While the present disclosure makes reference to certain embodiments, numerous modifications, alterations, and changes to the described embodiments are possible without departing from the sphere and scope of the present disclosure, as defined in the appended claims. Accordingly, it is intended that the present disclosure not be limited to the described embodiments, but that it has the full scope defined by the language of the following claims, and equivalents thereof.

What is claimed is:

1. A method of assessing vagus nerve stimulation in congestive heart failure treatment of a subject patient, the method comprising:
   detecting a delivery of a stimulation signal from an implantable neurostimulator device in the subject patient, wherein detecting the delivery of the stimulation signal is performed by a wand assembly in communication with the implantable neurostimulator device; and
   synchronizing a start of a recording of an ECG response signal with the delivery of the stimulation signal delivery based upon the detection of the delivery of the stimulation signal by the wand assembly.

2. The method of claim 1, wherein the detecting includes indirectly detecting a communication transmission between a wand of the wand assembly and the neurostimulator.

3. The method of claim 2, wherein the indirectly detecting includes detecting the communication transmission with a parallel capacitor and resistor of a detection circuit.

4. The method of claim 3, wherein the detection circuit includes an inductor, and wherein the indirectly detecting includes detecting, by the inductor, a pulse indicating a time of an initiating pulse of the stimulation signal.

5. The method of claim 4, wherein the indirectly detecting includes detecting a voltage induced across the inductor by the pulse, the induced voltage exceeding a threshold to indicate the time of the initiating pulse.

6. The method of claim 5, wherein the detection circuit includes a low pass filter, and wherein the indirectly detecting includes defining the threshold by the low pass filter.

7. The method of claim 1, wherein the synchronizing includes identifying an ON-period and an OFF-period of the stimulation signal and distinguishing first portions of the ECG response signal corresponding to the ON-period from second portions corresponding to the OFF-period.

8. The method of claim 7, further comprising:
   detecting each QRS complex in each of the first portions and the second portions of the recorded ECG signal;
   identifying each potential R-wave in each QRS complex;
   determining a time interval between each pair of successive R-waves; and
   determining an instantaneous heart rate for each determined time interval.

9. The method of claim 1, further comprising:
   acquiring, by a lead assembly, an analog ECG signal of the subject patient over a plurality of ON-periods and OFF-periods of the stimulation signal, and wherein the detecting includes generating, by the wand assembly, an analog delivery detection signal indicating delivery of the stimulation signal; and
   capturing and converting, by a data acquisition system coupled to the wand and lead assemblies, each of the analog ECG signal and the analog delivery detection signal to a digital ECG signal and a digital delivery detection signal.

10. The method of claim 1, wherein the wand assembly includes a programming device configured to wirelessly communicate with the implantable neurostimulator device and a cable connector configured to form a surface contact with the programming device, the cable connector including a detection circuit; and
   wherein the detecting includes indirectly detecting a time of an initiating pulse of the stimulation signal via the detection circuit.

* * * * *